(12) United States Patent
Novikov et al.

(10) Patent No.: US 7,252,830 B2
(45) Date of Patent: Aug. 7, 2007

(54) MOISTURIZING COMPOSITIONS

(75) Inventors: Alexander Novikov, Framingham, MA (US); Stephen Thong, Needham, MA (US); Janet Kelley O'Grady, Westwood, MA (US)

(73) Assignee: The Gillette Company, Boston, MA (US)

( * ) Notice: Subject to any disclaimer, the term of this patent is extended or adjusted under 35 U.S.C. 154(b) by 216 days.

(21) Appl. No.: 10/679,738

(22) Filed: Oct. 6, 2003

(65) Prior Publication Data

US 2005/0074472 A1   Apr. 7, 2005

(51) Int. Cl.
*A61K 8/00* (2006.01)
*A61K 8/18* (2006.01)
*A61K 8/02* (2006.01)
*A61K 9/127* (2006.01)
*A61Q 17/04* (2006.01)

(52) U.S. Cl. ............... 424/401; 424/59; 424/450
(58) Field of Classification Search ........ 424/59, 424/401, 450
See application file for complete search history.

(56) References Cited

U.S. PATENT DOCUMENTS

| 4,217,344 | A |   | 8/1980  | Vanlerberghe et al. | 424/60 |
| 4,246,285 | A | * | 1/1981  | Van Duzee | 514/788 |
| 5,260,065 | A |   | 11/1993 | Mathur et al. | 424/450 |
| 5,439,967 | A |   | 8/1995  | Mathur | |
| 5,474,848 | A |   | 12/1995 | Wallach | 428/402.2 |
| 5,616,334 | A |   | 4/1997  | Janoff et al. | 424/404 |
| 5,641,493 | A | * | 6/1997  | Date et al. | 424/401 |
| 5,643,600 | A |   | 7/1997  | Mathur | 424/450 |
| 5,756,014 | A |   | 5/1998  | Mathur | |
| 5,846,551 | A |   | 12/1998 | Dacunha et al. | 424/401 |
| 6,068,847 | A |   | 5/2000  | Aleles et al. | 424/401 |
| 6,251,425 | B1 |  | 6/2001  | Mathur | 424/450 |
| 6,296,857 | B1 | * | 10/2001 | Schonrock et al. | 424/401 |
| 6,309,663 | B1 | * | 10/2001 | Patel et al. | 424/450 |
| 6,368,607 | B1 |  | 4/2002  | Rerek et al. | 424/401 |
| 6,541,018 | B1 |  | 4/2003  | Simonnet et al. | 424/401 |

FOREIGN PATENT DOCUMENTS

| WO | WO 93/05767 | 4/1993 |
| WO | WO 95/13051 | 5/1995 |
| WO | WO 95/16436 | 6/1995 |
| WO | WO 98/46348 | 10/1998 |
| WO | WO 99/38486 | 8/1999 |
| WO | WO 00/19980 | 4/2000 |

OTHER PUBLICATIONS

Main World Sources of Oils Soya oil http://web.archive.org/web/20041019234701/http://ww.cyberlipid.org pp. 1-6.*

* cited by examiner

*Primary Examiner*—Johann Richter
*Assistant Examiner*—Ernst Arnold
(74) *Attorney, Agent, or Firm*—Andrew J. Hagerty; Tara M. Rosnell; Brian M. Bolam

(57) ABSTRACT

Moisturizing compositions containing bilayered vesicles, e.g., microvesicles, are provided. In some implementations, the vesicles include an ethoxylated polyol ester of a fatty acid, a sterol, and a long chain fatty alcohol.

25 Claims, No Drawings

MOISTURIZING COMPOSITIONS

TECHNICAL FIELD

This invention relates to moisturizing compositions for use in skin care, and more particularly to moisturizing lotions.

BACKGROUND

A wide variety of moisturizing lotions ("moisturizers") are available to consumers. Many of these moisturizers are emulsions that contain relatively high levels of lipophilic materials, such as oils, emollients, lipophilic emulsifiers and/or fatty polyols. Moisturizers containing such ingredients may have a tacky feel, and/or poor "rub-in" properties, i.e., the moisturizer will tend to leave a noticeable residue or film on the skin surface, rather than being readily absorbed.

Attempts to improve the skin-feel and rub-in properties of such emulsions have generally focused on reducing the particle size of the droplets in the emulsion, e.g., by forming micro- or nano-emulsions. Micro-emulsions typically require relatively large amounts of emulsifiers and/or surfactants to provide emulsion stability—ingredients which may potentially cause skin irritation—while formation of nano-emulsions may require high shear or phase inversion temperature processing, which may limit the range of ingredients that can be included in the moisturizer.

Some cosmetic formulations include phospholipids to provide a combination of moisturizing properties and good aesthetic properties, e.g., skin-feel and rub-in. While phospholipids provide a good balance of properties, they are generally relatively expensive, and may pose shelf stability issues under some storage conditions.

SUMMARY

The present invention provides moisturizing compositions containing multi-layered vesicles, e.g., microvesicles. The use of such vesicles as the moisturizing component of the compositions provides a good balance of moisturizing properties and desirable aesthetic properties such as good rub-in and good skin after-feel (i.e., skin feels smooth and hydrated). Preferred compositions are relatively low cost, and can be produced using conventional mixing and homogenization techniques, without the need for excessively high shear or the use of deleteriously high levels of skin-irritating surfactants or emulsifiers. The use of preferred vesicles allows a wide range of skin care actives, including water- and oil-soluble ingredients, to be delivered to the user without compromising moisturization or aesthetic properties.

The invention features moisturizing compositions including 60% to 90% water, and, as a moisturizing active, a plurality of bilayered microvesicles.

In one aspect, the bilayered microvesicles include an ethoxylated polyol ester of a fatty acid, a sterol, and a long chain fatty alcohol.

In another aspect, the bilayered microvesicles include an ethoxylated polyol ester of a fatty acid, a sterol, and a long chain fatty alcohol in a ratio in the range of about 1.0:0.4:1.7 to 1.0:0.3:1.2, and each of the bilayered microvesicles includes a plurality of bi-layers.

In a further aspect, the invention features a method of making a moisturizing composition including combining an aqueous phase and a lipid phase, the lipid phase including an ethoxylated polyol ester of a fatty acid, a sterol, and a long chain fatty alcohol, under sufficient agitation to form an emulsion.

The ingredients may be heated prior to or during the combining step. The combining step may include first blending the ethoxylated polyol ester of a fatty acid, the sterol, and the long chain fatty alcohol and any other components of the lipid phase to form a mixture, and then adding the aqueous phase to the mixture.

The details of one or more embodiments of the invention are set forth in the accompanying drawings and the description below. Other features and advantages of the invention will be apparent from the description and drawings, and from the claims.

DETAILED DESCRIPTION

Preferred moisturizing compositions include water, and, as a moisturizing active, a plurality of bilayered microvesicles composed of an ethoxylated polyol ester of a fatty acid, a sterol, and a long chain fatty alcohol. These components together define an emulsification system.

Some preferred compositions may also include other ingredients, for example a stabilizer, a skin care active such as a vitamin, anti-irritant or sunscreen, and/or one or more emollients. In some implementations the composition may also include a thickener.

By "bilayered microvesicles," we mean spherical structures having one or more bi-layers, each bi-layer being composed of amphiphilic materials (i.e., materials having both hydrophilic and lipophilic properties) aligned in two parallel rows. The lipophilic portions of each row are aligned towards each other, forming a bilayer interface, and the hydrophilic portions are aligned away from the bilayer interface. Where there are multiple bilayers, adjacent hydrophilic portions are positioned towards each other.

When included in an otherwise similar formulation, preferred microvesicles provide moisturizing and aesthetic properties comparable to those that are typically provided by phospholipids. The microvesicles typically have a particle size of less than about 1 micron, preferably from about 100 nm to 1 micron The bilayered microvesicles are formed using three basic ingredients: (a) an ethoxylated polyol ester of a fatty acid, (b) a sterol, and (c) a long chain fatty alcohol. These ingredients will be discussed in detail below. Because of the use of this combination of ingredients, the microvesicles can be formed without high shear. Preferably, the microvesicles are formed by blending these ingredients together, along with any other lipophilic ingredients of the composition, and combining the resulting lipophilic mixture with the water and any other aqueous ingredients under adequate agitation (e.g., using a Heidolph-Brinkmann Lab Mixer with a square blade impeller at 120 to 150 rpm) to form an emulsion. It is generally preferred that the lipophilic and aqueous components be heated prior to or during mixing and emulsification to facilitate these processes. Heating temperatures will vary depending on the ingredients used, but are typically in the range of 50-100° C., e.g., about 75° C. After emulsification, the emulsion may be homogenized, e.g., for about 2 minutes at about 55° C. using a standard overhead homogenizer. Temperature sensitive materials, e.g., vitamins, preservatives, fragrances, botanical extracts, and essential oils may be added and mixed in under lower temperature and low shear conditions, after the emulsification and homogenization steps described above have been completed. A brief further homogenization step can be performed after all ingredients have been added.

The ethoxylated polyol ester of a fatty acid generally functions as a primary emulsifier, allowing the three ingredients to form an oil-in-water emulsion under relatively low shear conditions. The ethoxylated polyol ester of a fatty acid has a polyol (polyhydric alcohol) backbone, in which one of the hydroxy groups on the polyol is replaced with a fatty acyl group and another of the hydroxy groups on the polyol is replaced with a polyethoxy ether group. Suitable polyols (polyhydric alcohols) include those having 3 to 6 carbon atoms and 2 to 6 hydroxy groups such as, for example, glycerine, butylene glycol, pentylene glycol, propylene glycol and mixtures thereof. Suitable fatty acyl groups will have a medium fatty acyl chain length, such as C10 to C16, preferably C12. A suitable ethoxylation range is about 7 to 30 ethoxy units, preferably 20 units. An example of a suitable ethoxylated polyol ester of a fatty acid is PEG-20 glyceryl laurate. Typically, the composition includes from about 0.5% to 15.0% of the ethoxylated polyol ester of a fatty acid, preferably about 1% to 3% and more preferably about 1.6% to 2%.

The sterol generally functions as a stabilizer, enhancing the stability of the microvesicles, and also provides moisturizing properties. Suitable sterols include cholesterol, phytosterols such as soya glycine sterol, and lanosterol, as well as mixtures of two or more of these sterols. Typically, the composition includes from about 0.5% to 10.0% of the sterol, preferably about 0.5% to 5%, more preferably about 0.5% to 1%, and most preferably about 0.6% to 0.8%.

The long chain fatty alcohol generally functions as a "wall builder," forming the membrane walls of the vesicle and providing moisturizing properties. Preferred fatty alcohols generally have chain lengths of C16 to C30, preferably C18 to C24. Suitable fatty alcohols include stearyl alcohol, arachidyl alcohol, lignoceryl alcohol, behenyl alcohol and mixtures of two or more of these alcohols. Typically, the composition includes from about 0.5% to 20% of the fatty alcohol, preferably about 1% to 10% and more preferably about 2% to 3%.

Preferably, the ethoxylated polyol ester of a fatty acid, the sterol and the long chain fatty alcohol are provided in a ratio in the range of about 1:0.2-0.5:1-2, preferably 1:0.3-0.4:1.2-1.7. The ratio is selected to ensure adequate emulsification of the hydrophobic ingredients and to achieve structural stability of the emulsion, as well as to provide the product with sufficient "body" and a cosmetic feel.

Additional amphiphiles that may be a part of the bilayers include the following: monoesters of polyols, e.g., glyceryl monoesters, propylene glycol monoesters, sorbitan monoesters and sucrose monoesters; other low HLB ethoxylated fatty alcohols, e.g., ethoxylated fatty alcohols having 2-4 ethoxy units and a fatty chain length of C12-18; fatty amides, e.g., stearoylamide and cocoamide; and phospholipids. Generally, the composition may include about 0.1% to 10.0% of such additional amphiphiles.

Suitable skin care actives include oil and water soluble vitamins; anti-irritants, e.g., bisabolol and glycyrrhyzinic acid; and organic and inorganic sunscreens, e.g., octyl methoxycinnamate, benzophenone, avobenzone, octyl salicylate, homosalate, titanium dioxide and zinc oxide. In some implementations the composition will include from about 0.1 to 20% total skin care actives. If it is desired that the composition have an SPF of 15, the composition will typically include from about 7 to 13% of an organic sunscreen, or about 5 to 10% of an organic sunscreen and about 0 to 3% of an inorganic sunscreen. Suitable emollients include esters of linear or branched fatty alcohols and fatty acids with a fatty acyl chain length of from C6 to C14, e.g., isononyl isonanoate, dioctyl sebacate, isooctyl isooctanoate, and dioctyl adipate; hydrocarbons, e.g., squalane, petrolatum and mineral oil; natural waxes, e.g., carnauba wax, candelilla wax, and beeswax; vegetable oils, e.g., sunflower oil, sesame oil and olive oil; and silicones, e.g. cyclomethicone and dimethicone. The composition may include any desired amount of these ingredients that will not deleteriously effect the performance, aesthetics or stability of the composition, typically from about 0 to 20%, preferably about 0.5 to 5%, more preferably about 1 to 2%.

In some implementations the composition may also include a water-soluble thickener, e.g. polyacrylamide, polysaccharide and/or oil-soluble thickener, e.g., pentaerythrityl tetrastearate. The composition may further include other conventional cosmetic ingredients such as preservatives, colorants, fragrances and essential oils.

Sufficient water is included to provide an emulsion and give the composition a desired viscosity. Preferred compositions generally include from about 60 to 90% water, which will typically produce a light cream having a viscosity (Brookfield Viscosimeter, RVT spindle # 5, 10 rpm, 5th revolution) from about 10,000 to 30,000 cps under the processing conditions described above.

The percentages given above are percentages by weight, on a solids basis.

EXAMPLE

A composition was prepared having the following formulation:

| Ingredient | Weight % |
|---|---|
| Water | 78.2750 |
| Octyl Methoxycinnamate | 5.0000 |
| Cyclomethicone | 3.0000 |
| Isononyl Isononanoate | 3.0000 |
| Benzophenone-3 | 2.0000 |
| Polyacrylamide & C13–14 Isoparaffin & Laureth-7 | 1.4000 |
| PEG-20 Glyceryl Laurate | 1.8000 |
| Behenyl Alcohol | 1.1300 |
| Stearyl Alcohol | 1.1200 |
| Arachidyl Alcohol | 0.2500 |
| Cholesterol | 0.7000 |
| Glyceryl Stearate | 1.0000 |
| Dimethicone | 0.7500 |
| Lecithin | 0.2000 |
| Disodium EDTA | 0.0500 |
| Preservative | 0.3000 |
| Fragrance | 0.0250 |

Lipophilic materials were mixed together and heated to 75° C. to provide a clear lipid blend. Water and the temperature stable solutes were heated to 75° C. The oil and aqueous phases were then combined with adequate agitation and maintained at 75° C. for 30 min. The resulting oil-in-water emulsion was then cooled to 55° C. and homogenized briefly (2 min) using a standard overhead homogenizer.

Under examination using light microscopy, the resulting emulsion appeared as microvesicles of less than 500 nm diameter. Temperature-sensitive materials (vitamins, preservatives, fragrances, botanical extracts, essential oils) were then added at 40° C. with agitation. Silicones were added at 40° C., followed by addition of thickener and brief homogenizing (2 min). At room temperature the product had the appearance of a white light cream having a viscosity of 15,000-30,000 cps.

A number of embodiments of the invention have been described. Nevertheless, it will be understood that various modifications may be made without departing from the spirit and scope of the invention. Accordingly, other embodiments are within the scope of the following claims.

What is claimed is:

1. A moisturizing composition comprising:
   60% to 90% water, and
   as a moisturizing active component, a plurality of bilayered microvesicles;
   wherein the bilayered microvesicles comprise an ethoxylated acyclic polyol ester of a fatty acid having a fatty acyl chain length of C10 to C16, a sterol, and a long chain fatty alcohol, and
   wherein the ratio of ethoxylated acylic polyol ester of a fatty acid, to sterol, to long chain fatty alcohol, is in the range of 1:0.2-0.5:1-2.

2. The composition of claim 1 further comprising a skin care active component.

3. The composition of claim 2 wherein the skin care active component is selected from the group consisting of vitamins, anti-irritants and sunscreens.

4. The composition of claim 1 further comprising one or more emollients.

5. The composition of claim 1 wherein each of the bilayered microvesicles includes a plurality of bi-layers.

6. The composition of claim 1 comprising 0.5% to 15% ethoxylated acyclic polyol ester of a fatty acid, 0.5% to 10% sterol, and 0.5% to 20% long chain fatty alcohol.

7. The composition of claim 1 wherein the bilayered microvesicles have a particle size of about 100 nm to 1 micron.

8. The composition of claim 1 wherein the ethoxylated acyclic polyol ester of a fatty acid has an ethoxylation range of about 7 to 30 ethoxy units.

9. A moisturizing composition comprising:
   60% to 90% water, and
   as a moisturizing active component, a plurality of bilayered microvesicles;
   wherein the bilayered microvesicles comprise an ethoxylated acyclic polyol ester of a fatty acid, a sterol, and a long chain fatty alcohol, and wherein the ethoxylated acyclic polyol ester of a fatty acid comprises PEG-20 glyceryl laurate.

10. The composition of claim 1 wherein the sterol is selected from the group consisting of cholesterol, phytosterols, lanosterol and mixtures thereof.

11. The composition of claim 10 wherein the long chain fatty alcohol is selected from the group consisting of stearyl alcohol, arachidyl alcohol, behenyl alcohol and mixtures thereof.

12. The composition of claim 1 wherein the long chain fatty alcohol has a chain length of C16-C30.

13. The composition of claim 12 wherein the long chain fatty alcohol is selected from the group consisting of stearyl alcohol, arachidyl alcohol, lignoceryl alcohol, behenyl alcohol and mixtures thereof.

14. The composition of claim 1 wherein the ratio of ethoxylated acyclic polyol ester of a fatty acid, to sterol, to long chain fatty alcohol, is in the range of 1:0.3-0.4:1.2-1.7.

15. The composition of claim 1 further comprising an amphiphile selected from the group consisting of monoesters of polyols, low HLB ethoxylated fatty alcohols, fatty amides. and phospholipids.

16. The composition of claim 15 wherein the composition comprises from about 0.1 to 10% of said amphiphile.

17. The composition of claim 1, wherein the acyclic polyol is selected from the group consisting of glycerine, butylene glycol, pentylene glycol, propylene glycol and mixtures thereof.

18. The composition of claim 2, wherein said skin care active component is selected from the group consisting of oil and water soluble vitamins, anti-irritants, and organic and inorganic sunscreens.

19. The composition of claim 1 Farther comprising a sunscreen selected from the group consisting of octyl methoxycinnamate, benzophenone, avobenzone, octyl salicylate, homosalate, titanium dioxide and zinc oxide.

20. The composition of claim 1 further comprising an emollient.

21. The composition of claim 20 wherein the emollient is selected from the group consisting of esters of linear or branched fatty alcohols and fatty acids with a fatty acyl chain length of from C6 to C14, hydrocarbons, natural waxes, vegetable oils, and silicones.

22. The composition of claim 20 wherein the composition comprises from about 0.5 to 5% of said emollient.

23. The composition of claim 1 further comprising a water-soluble thickener.

24. A moisturizing composition comprising:
   60% to 90% water, and
   as a moisturizing active component, a plurality of bilayered microvesicles:
   wherein the bilayered microvesicles comprise an ethoxylated acyclic polyol ester of a fatty acid, a sterol. and a long chain fatty alcohol, and
   wherein the ratio of ethoxylated acyclic polyol ester of a fatty acid, to sterol, to long chain fatty alcohol, is in the range of 1:0.2-0.5:1-2.

25. The composition of claim 24 wherein the ratio of ethoxylated acyclic polyol ester of a fatty acid, to sterol. to long chain fatty alcohol, is in the range of 1:0.3-0.4:1.2-1.7.

* * * * *